United States Patent
Jolly

(10) Patent No.: US 8,150,528 B2
(45) Date of Patent: Apr. 3, 2012

(54) DOUBLE BRANCH COCHLEAR IMPLANT ELECTRODE

(75) Inventor: Claude Jolly, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 394 days.

(21) Appl. No.: 12/559,665

(22) Filed: Sep. 15, 2009

(65) Prior Publication Data

US 2010/0069999 A1    Mar. 18, 2010

Related U.S. Application Data

(60) Provisional application No. 61/097,343, filed on Sep. 16, 2008.

(51) Int. Cl.
*A61N 1/00* (2006.01)

(52) U.S. Cl. ......................................................... 607/57

(58) Field of Classification Search .................... 607/56, 607/57, 137
See application file for complete search history.

(56) References Cited

U.S. PATENT DOCUMENTS

| | | | |
|---|---|---|---|
| 4,261,372 A | 4/1981 | Hansen et al. | 607/137 |
| 4,686,765 A * | 8/1987 | Byers et al. | 29/858 |
| 5,876,443 A | 3/1999 | Hochmair et al. | 623/10 |
| 5,922,017 A | 7/1999 | Bredberg et al. | 607/137 |
| 5,999,859 A | 12/1999 | Jolly | 607/137 |
| 6,231,604 B1 | 5/2001 | Von Ilberg | 623/10 |
| 6,377,849 B1 | 4/2002 | Lenarz et al. | 604/21 |
| 6,487,453 B1 | 11/2002 | Kuzma et al. | 607/137 |
| 6,549,814 B1 * | 4/2003 | Strutz et al. | 607/137 |
| 6,556,870 B2 | 4/2003 | Zierhofer et al. | 607/57 |
| 2002/0082554 A1 | 6/2002 | Lenarz et al. | 604/104 |
| 2006/0212094 A1 * | 9/2006 | Moser et al. | 607/57 |
| 2007/0005117 A1 * | 1/2007 | Fritsch et al. | 607/56 |

FOREIGN PATENT DOCUMENTS

| WO | WO 93/06698 | 4/1993 |
|---|---|---|
| WO | WO 00/69513 | 11/2000 |

OTHER PUBLICATIONS

European Patent Office, International Search Report and Written Opinion, PCT/IB2009/007947, Apr. 21, 2010.

* cited by examiner

*Primary Examiner* — George Manuel
*Assistant Examiner* — Robert Wieland
(74) *Attorney, Agent, or Firm* — Sunstein Kann Murphy & Timbers LLP

(57) ABSTRACT

A stimulation electrode is described for a hearing impaired patient. An intra-fluid electrode branch is immersed in cochlear fluid within an interior volume of a patient cochlea and has electrode contacts for delivering a cochlear stimulation signal to adjacent neural tissue. An intra-modiolus electrode branch penetrates through the cochlea and has one or more electrode contacts for delivering a modiolus stimulation signal to cochlear nerve tissue within the modiolus of the patient.

12 Claims, 6 Drawing Sheets

DOUBLE BRANCH COCHLEAR IMPLANT ELECTRODE

This application claims priority from U.S. Provisional Patent Application 61/097,343, filed Sep. 16, 2008, which is incorporated herein by reference.

FIELD OF THE INVENTION

The present invention relates to medical implants, and more specifically to an implantable electrode for use in cochlear implant systems.

BACKGROUND ART

A normal ear transmits sounds as shown in FIG. 1 through the outer ear 101 to the tympanic membrane (eardrum) 102, which moves the bones of the middle ear 103 (malleus, incus, and stapes), which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses that are transmitted to the cochlear nerve 113, and ultimately to the brain.

Hearing is impaired when there are problems in the ability to transduce external sounds into meaningful action potentials along the neural substrate of the cochlea 104. For example, in some patients, the cochlear shape fails to develop properly and various malformation conditions can occur such as those shown in FIG. 2: cochlear aplasia, cochlear hypoplasia, common cavity malformation, and incomplete partitioning.

A cochlear implant is an auditory prosthesis which uses an implanted stimulation electrode to bypass the acoustic transducing mechanism of the ear and instead stimulate auditory nerve tissue directly with small currents delivered by multiple electrode contacts distributed along the electrode. FIG. 1 also shows some components of a typical cochlear implant system which includes an external microphone that provides an audio signal input to an external signal processing stage 111 where various signal processing schemes can be implemented. The processed signal is then converted into a digital data format, such as a sequence of data frames, for transmission into the implant stimulator 108. Besides extracting the audio information, the implant stimulator 108 also performs additional signal processing such as error correction, pulse formation, etc., and produces a stimulation pattern (based on the extracted audio information) that is sent through connected wires 109 to an implanted electrode carrier 110. Typically, this electrode carrier 110 includes multiple electrodes on its surface that provide selective stimulation of the cochlea 104.

Cochlear implant systems need to deliver electrical power from outside the body through the skin to satisfy the power requirements of the implanted portion of the system. As shown in FIG. 1, an external transmitter coil 107 (coupled to the external signal processor 111) is placed on the skin adjacent to a subcutaneous receiver coil connected to the implant stimulator 108. Often, a magnet in the external coil structure interacts with a corresponding magnet in the subcutaneous secondary coil structure. This arrangement inductively couples a radio frequency (rf) electrical signal to the implant stimulator 108. The implant stimulator 108 is able to extract from the rf signal both the audio information for the implanted portion of the system and a power component to power the implanted system.

When the cochlea is severely ossified, double branch intra-scala electrodes have been used as shown in FIG. 3, where an ossified cochlea 301 receives two intra-scala electrodes 301 and 302 for stimulating auditory nerve tissue in different sections of the cochlea 301. As shown, this approach requires two cochleostomies for the electrode insertions. For a fuller discussion of this subject, see, for example, U.S. Pat. No. 5,922,017, which is incorporated herein by reference.

In the case of malformed cochleas such as the ones illustrated in FIG. 2, there may be some neural tissue present within the cochlear volume. In such cases, both conventional single branch and double branch multi-contact electrodes have been inserted into the cochlear fluid in the existing cavity and electrical stimulation signals applied. Similarly, in incomplete partition cochleas, conventional multi-contact electrodes have been used, usually having a shorter length.

SUMMARY OF THE INVENTION

Embodiments of the present invention are directed to a stimulation electrode for a hearing impaired patient. An intra-fluid electrode branch is immersed in cochlear fluid within an interior volume of a patient cochlea and has electrode contacts for delivering a cochlear stimulation signal to adjacent neural tissue. An intra-modiolus electrode branch penetrates through the cochlea and has one or more electrode contacts for delivering a modiolus stimulation signal to cochlear nerve tissue within the modiolus of the patient.

In further specific embodiments, the stimulation electrode may include an electrode trunk with a basal end connected to an implantable stimulation module and an apical end having the electrode branches. The intra-modiolus electrode branch may include a penetrating shank. The intra-modiolus electrode branch may have just one single electrode contact; for example, a ball contact. Or the intra-modiolus electrode branch may include multiple electrode contacts. The intra-modiolus electrode branch may be based on a thin film electrode. The intra-modiolus electrode approach or penetrate into the cochlea nerve tissue within the modiolus. The interior volume may include the scala tympani of a patient cochlea or a common cavity of a malformed patient cochlea.

Embodiments also include a complete cochlear implant system having a stimulation electrode according to any of the above.

DETAILED DESCRIPTION OF SPECIFIC EMBODIMENTS

Figure 1:
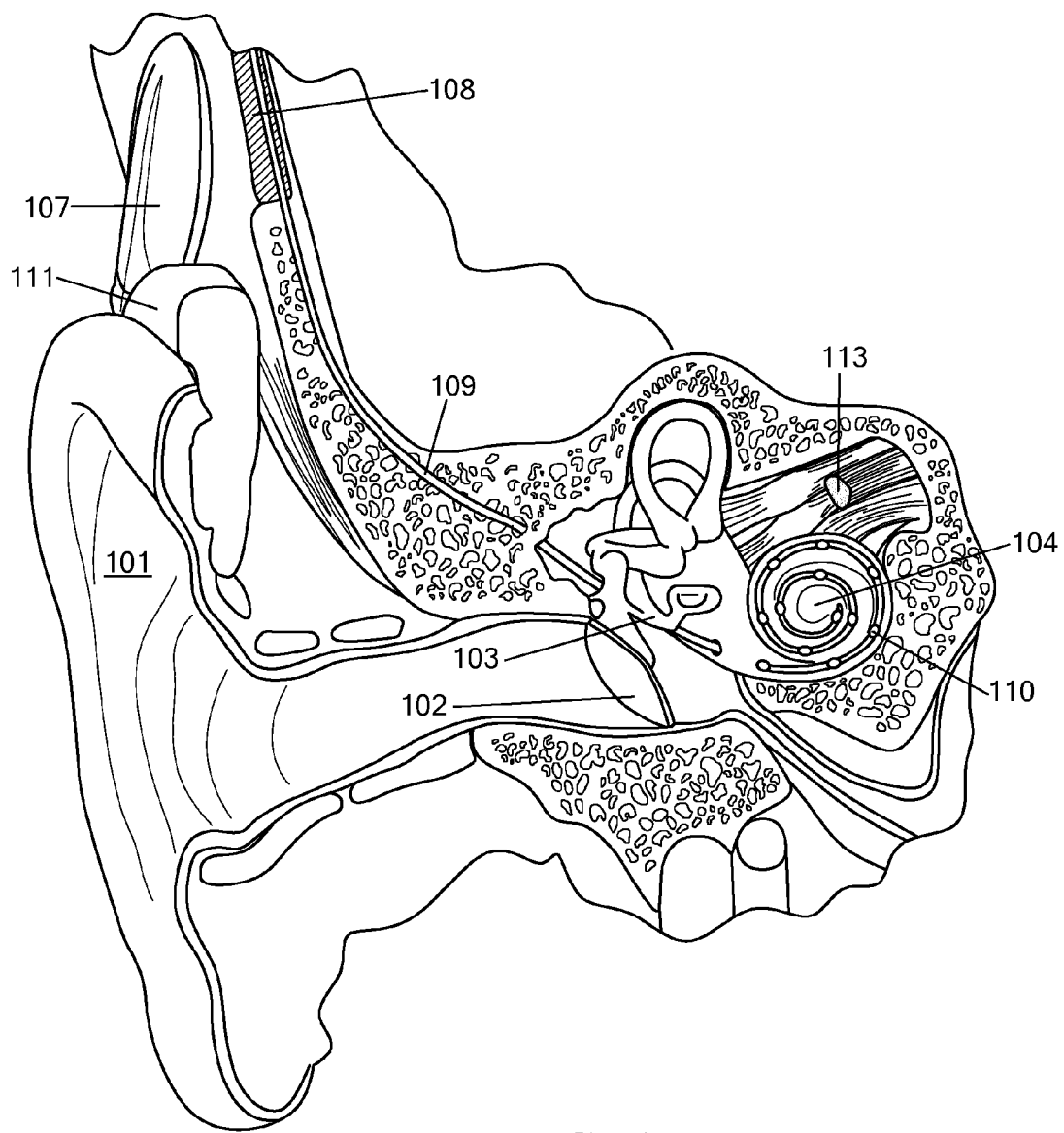
FIG. 1 shows elements of a human ear having a typical cochlear implant system.
Figure 2:
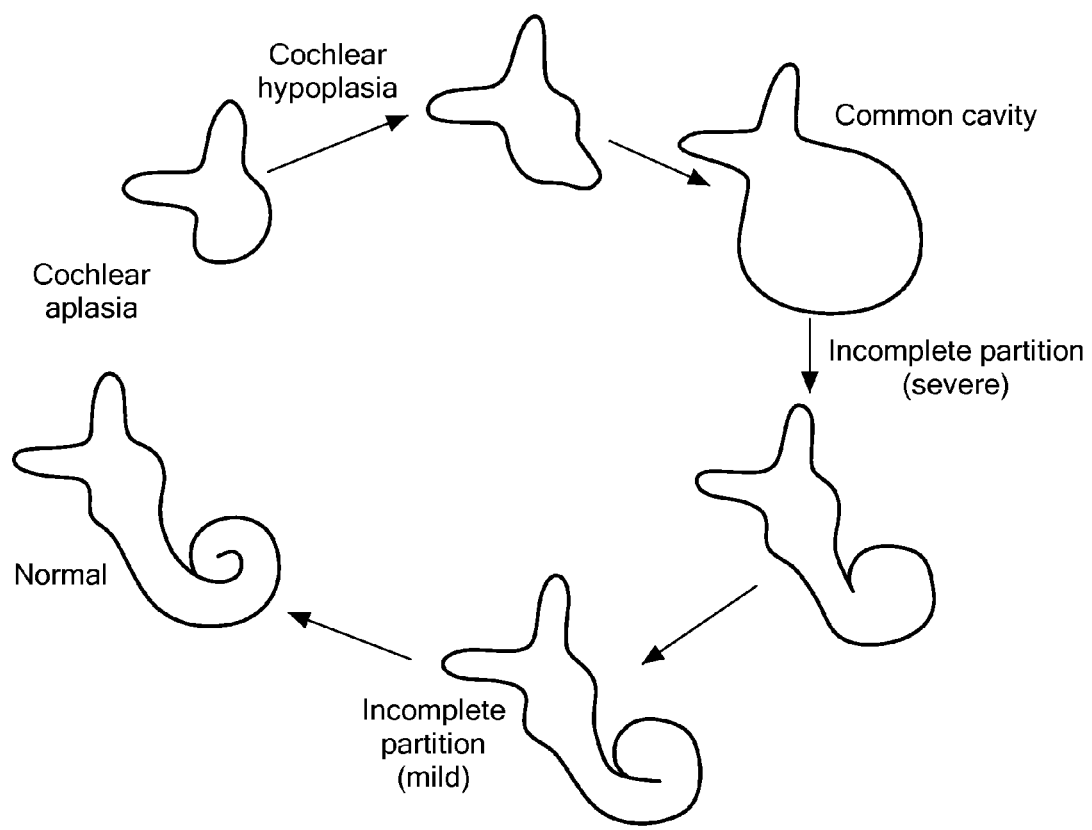
FIG. 2 illustrates various cochlear malformation shapes.
Figure 3:
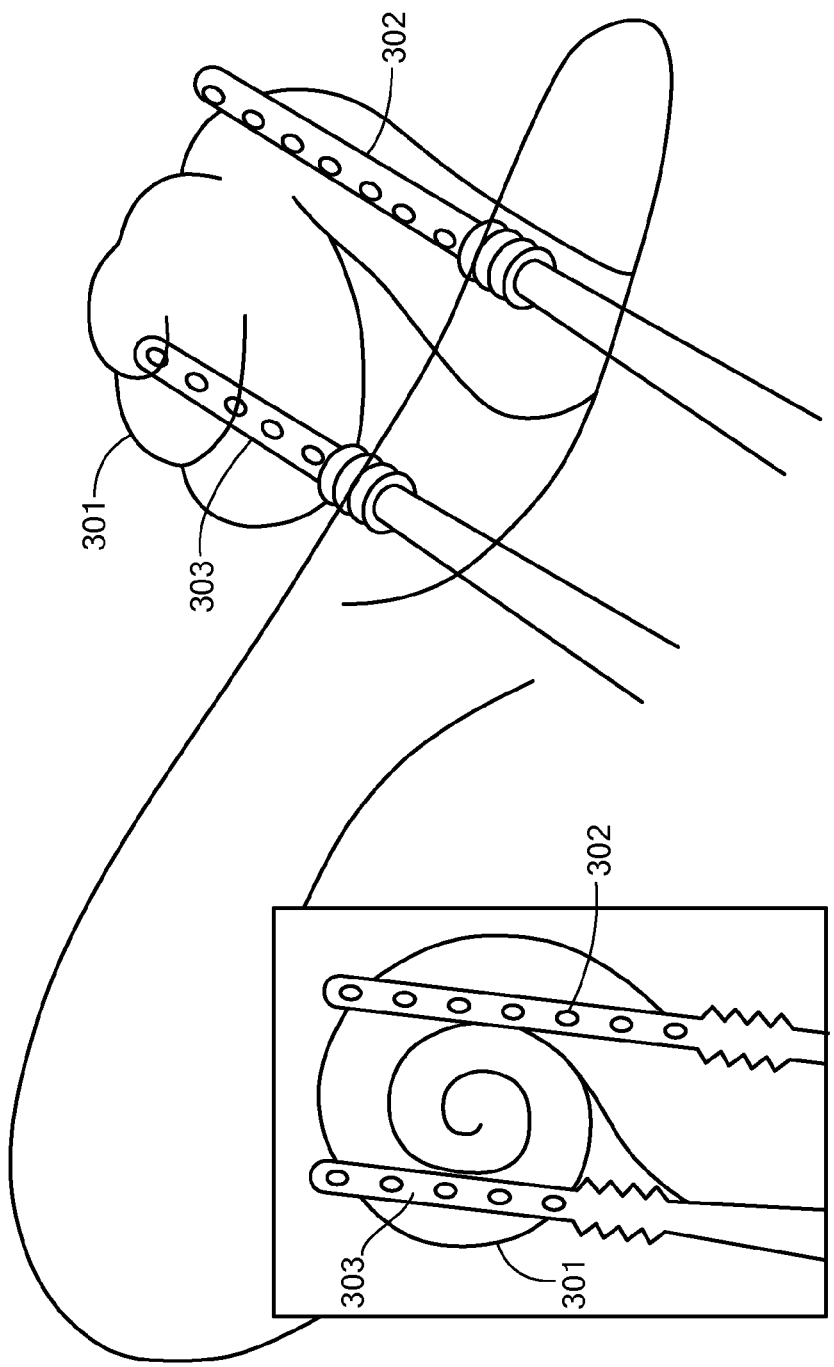
FIG. 3 shows use of a double branch intra-scala electrodes in an ossified cochlea.
Figure 4:
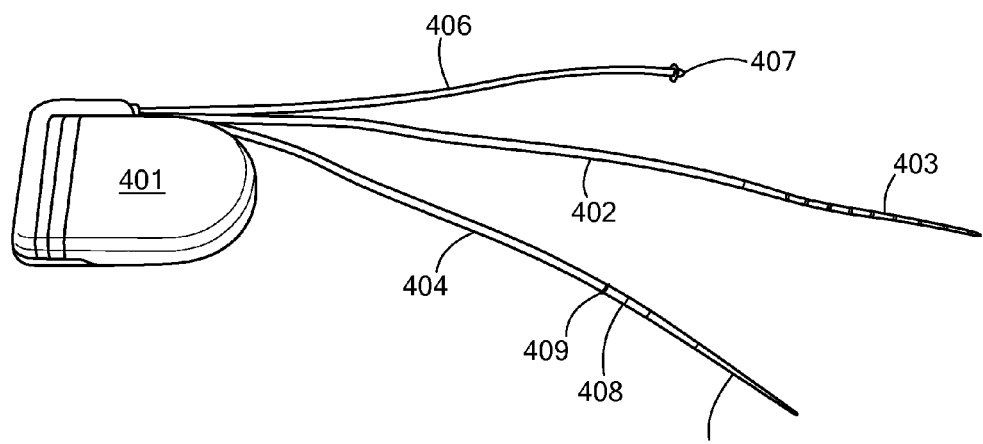
FIG. 4 shows an example of a double branch electrode according to one specific embodiment of the present invention.

Various embodiments of the present invention are directed to a stimulation electrode for a hearing impaired patient which has two different branches. FIG. 4 shows an example of a double branch electrode according to one specific embodiment of the present invention. An implant housing 401 generates and delivers a first set of electrical stimulation signals to a flexible intra-scala (i.e., intra fluid) electrode branch 402 which is immersed in cochlear fluid within an interior volume of a patient cochlea (i.e., the scala tympani of a patient cochlea or a common cavity of a malformed patient cochlea) and has multiple electrode contacts 403 for delivering a cochlear stimulation signal to adjacent neural tissue. The implant housing 401 also generates and delivers a second set of electrical stimulation signal to a flexible intra-modiolus electrode branch 404 which penetrates through the cochlea and has one or more electrode contacts 405 for delivering a modiolus stimulation signal to cochlear nerve tissue within the modiolus of the patient. Such an arrangement gives improved access to more neural tissue than for either type of electrode by itself, especially in the specific case of a cochlear malformation. Flexible ground branch 406 terminates with one or more ground electrodes 407 which complete the current path for the stimulation electrodes.

Figure 5:
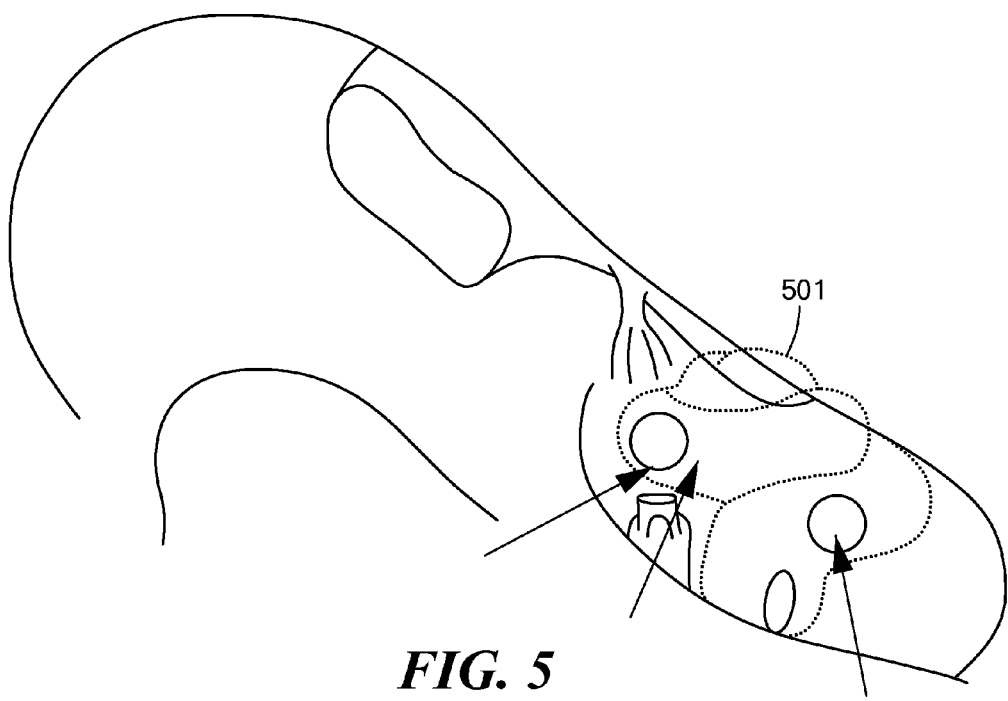
FIG. 5 shows some examples of the various directions for insertion of an intra-modiolus branch electrode.

Moreover, just a single cochleostomy can be performed at a single site as is done for a normal cochlear implant surgery, rather than a more complex surgery entailing two cochleostomies. The intra-modiolus electrode branch 404 can also be inserted through the same posterior tympanotomy as the intra scala electrode branch 402. Through a single cochleostomy, a thin penetrating intra-modiolus electrode branch 404 can be inserted close to or slightly through the modiolus at a specific angle of approach. In some situations, the cochleostomy may be enlarged slightly in a given direction to obtain a better angle of approach with respect to the auditory nerve in the modiolus. FIG. 5 shows some examples of the various directions for insertion of an intra-modiolus electrode branch 404 into a patient cochlea 501. One advantage of the dual electrode branch approach is that it is possible to approach very close to the modiolus and nerve trunk with or without penetrating it. One or two stimulation channels in such a strategic position could enhance system performance in a given patient. In some embodiments, the intra-modiolus branch electrode branch 404 may have one or more position markers 408 on it to indicate penetration depth into the modiolus or into the cochlear nerve. In this way penetration depth is controllable. A penetration stopper 409 on the intra-modiolus branch electrode branch 404 may also be useful to prevent over-penetration.

Figure 6:
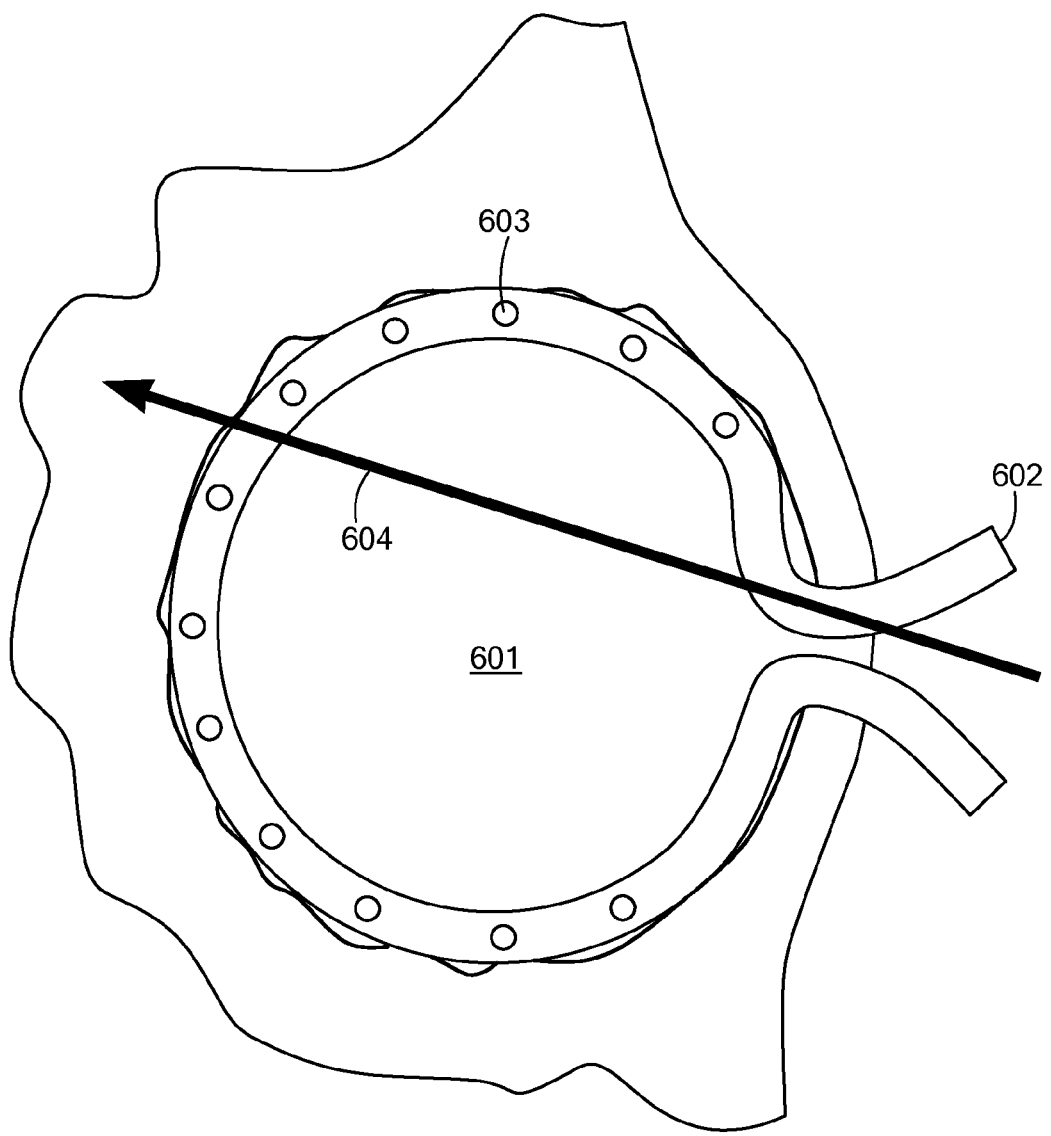
FIG. 6 illustrates the principle of an embodiment of a double branch electrode in a common cavity cochlea.

Embodiments of the present invention may be especially useful for researching intra-neural stimulation and/or for use in abnormal cochleas. For example, embodiments may be useful where this ossification of the middle to apical turn of the cochlea, or where there is partial basal ossification of the cochlea. A double branch electrode can also be useful in cases as shown in FIG. 6, of cochlear malformation such a common cavity cochlea 601 where some neural tissue lines the internal auditory canal which receives the penetrating intra-modiolus electrode branch 604, and some neural tissue also may be present within the common cavity 601 which is stimulated by the electrode contacts 603 on an intra-scala electrode branch 602. Double branch electrodes can also be used in severe to moderate incomplete partition cases giving access to more neural fibers than would be normally the case with just a single intra-scala electrode as in more typical cases.

Figure 7A:
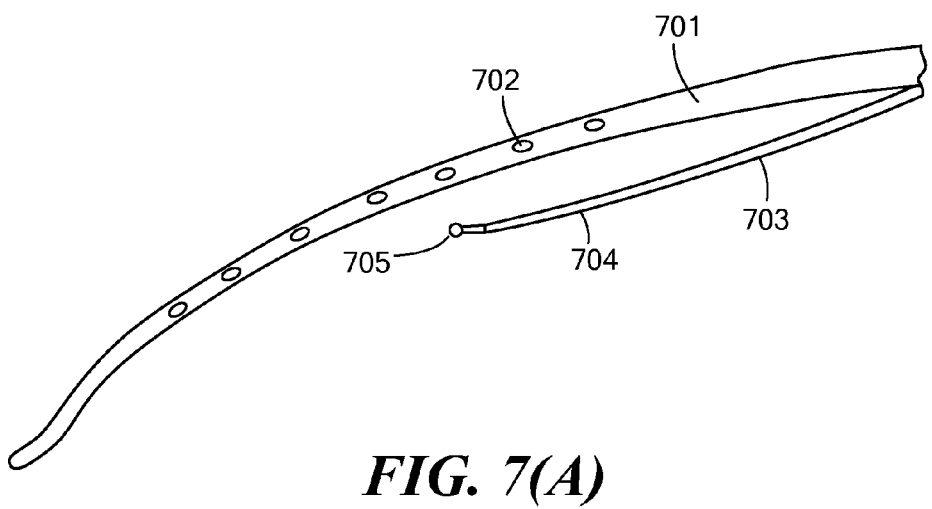
FIG. 7 A-B shows some details of various double branch electrodes.
Figure 7B:
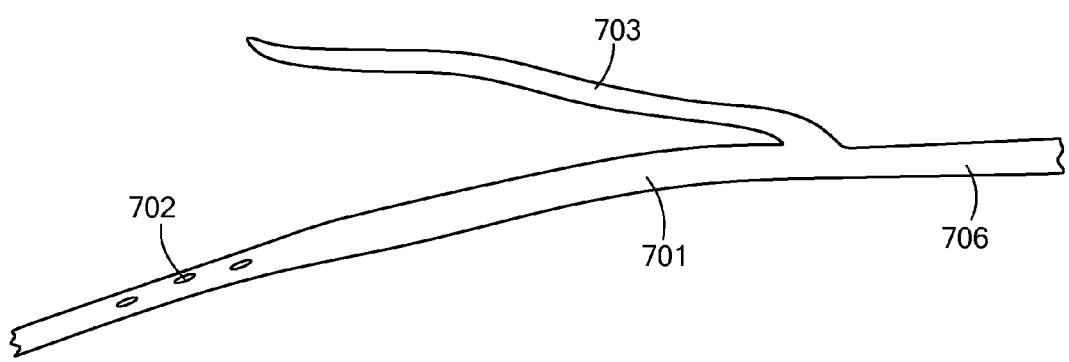

FIG. 7A shows an embodiment of a double branch electrode where an intra-modiolus electrode branch 703 terminates in a single ball contact 705 at the end of a penetrating shank 704 that approaches or penetrates nerve tissue within the modiolus. In other specific embodiments, the electrode contact on the intra-modiolus electrode branch 703 may be some other specific structure such as a cuff electrode that wraps around a portion of the auditory nerve in the modiolus after surgical implantation. FIG. 7B shows another embodiment where the dual branch electrode includes an electrode trunk 706 with a basal end connected to an implantable stimulation module and an apical end splitting into an intra-scala electrode branch 701 having multiple stimulation contacts 702 for stimulating nearby nerve tissue, and an intra-modiolus electrode branch 703 having at least one thin film electrode contact to stimulate neural tissue in modiolus. In some embodiments, an intra-modiolus electrode branch 703 may have multiple channels and multiple electrode contacts. For example, the penetrating shank 704 of the intra-modiolus electrode branch 703 may have at least two contacts, one for stimulation and the other for measuring the whole nerve action potential from the electrical stimulation triggering action potentials in the nerve tissue. It should be relatively easy to test system performance in such an embodiment by initially introducing the penetrating intra-modiolus electrode branch 703 near to the modiolus, and then depending on testing results from the measured whole nerve action potentials, the intra-modiolus electrode branch 703 may be pushed further into the modiolus nerve tissue to correctly position and reposition the intra-modiolus electrode branch for optimum patient response.

Although various exemplary embodiments of the invention have been disclosed, it should be apparent to those skilled in the art that various changes and modifications can be made which will achieve some of the advantages of the invention without departing from the true scope of the invention.

What is claimed is:

1. A stimulation electrode for a hearing impaired patient comprising:
    an intra-fluid electrode branch for immersion in cochlear fluid within an interior volume of a patient cochlea and having a plurality of electrode contacts for delivering a cochlear stimulation signal to adjacent neural tissue; and
    an intra-modiolus electrode branch for penetration through the cochlea and having at least one electrode contact for delivering a modiolus stimulation signal to cochlear nerve tissue within the modiolus of the patient.

2. A stimulation electrode according to claim 1, further comprising:
    an electrode trunk having a basal end connected to an implantable stimulation module and an apical end having the electrode branches.

3. A stimulation electrode according to claim 1, wherein the intra-modiolus electrode branch includes a penetrating shank.

4. A stimulation electrode according to claim 1, wherein the intra-modiolus electrode branch includes a single electrode contact for delivering the modiolus stimulation signal to the cochlear nerve tissue.

5. A stimulation electrode according to claim 4, wherein the single electrode contact is a ball contact.

6. A stimulation electrode according to claim 1, wherein the intra-modiolus electrode branch includes a plurality of electrode contacts for delivering the modiolus stimulation signal to the cochlear nerve tissue.

7. A stimulation electrode according to claim 1, wherein the intra-modiolus electrode branch is based on a thin film electrode.

8. A stimulation electrode according to claim 1, wherein the intra-modiolus electrode penetrates into the cochlea nerve tissue within the modiolus.

9. A stimulation electrode according to claim 1, wherein the intra-modiolus electrode approaches the cochlea nerve tissue within the modiolus.

10. A stimulation electrode according to claim 1, wherein the interior volume includes the scala tympani of a patient cochlea.

11. A stimulation electrode according to claim 1, wherein the interior volume includes a common cavity of a malformed patient cochlea.

12. A cochlear implant system having a stimulation electrode according to any of claims 1-11.

* * * * *